US009067069B2

(12) United States Patent
Svirsky

(10) Patent No.: US 9,067,069 B2
(45) Date of Patent: Jun. 30, 2015

(54) COCHLEAR IMPLANT FITTING SYSTEM

(71) Applicant: New York University, New York, NY (US)

(72) Inventor: Mario A. Svirsky, New York, NY (US)

(73) Assignee: NEW YORK UNIVERSITY, New York, NY (US)

(*) Notice: Subject to any disclaimer, the term of this patent is extended or adjusted under 35 U.S.C. 154(b) by 46 days.

(21) Appl. No.: 13/850,904

(22) Filed: Mar. 26, 2013

(65) Prior Publication Data

US 2013/0218237 A1    Aug. 22, 2013

Related U.S. Application Data

(63) Continuation-in-part of application No. 13/046,234, filed on Mar. 11, 2011, now abandoned, which is a continuation of application No. 12/128,312, filed on May 28, 2008, now Pat. No. 7,908,012.

(60) Provisional application No. 60/941,053, filed on May 31, 2007.

(51) Int. Cl.
*A61N 1/00*    (2006.01)
*A61N 1/36*    (2006.01)
*A61N 1/372*   (2006.01)

(52) U.S. Cl.
CPC ........ *A61N 1/36032* (2013.01); *A61N 1/37247* (2013.01)

(58) Field of Classification Search
CPC .......... A61N 1/36032; A61N 1/36132; A61N 1/37264
USPC ..................................................... 607/55–57
See application file for complete search history.

(56) References Cited

U.S. PATENT DOCUMENTS

2006/0100672 A1*  5/2006  Litvak ............................ 607/57
2014/0052217 A1*  2/2014  Smith ............................. 607/57

* cited by examiner

*Primary Examiner* — Scott Getzow
(74) *Attorney, Agent, or Firm* — Fay Kaplun & Marcin, LLP

(57) ABSTRACT

A system for electrically stimulating a first cochlear implant includes (a) an electrode contact simultaneously transmitting a first electrical stimulus from stimulation hardware to a first ear fitted with the first cochlear implant and a second stimulus from the stimulation hardware to a second ear, the second stimulus being one of electrical and acoustical; (b) a component establishing a plurality of frequency-to-electrode maps used to determine the first electrical stimulus; (c) a user-interface component permitting a user to adjust the frequency-to-electrode maps and receive the corresponding auditory stimulation in the first cochlear implant; (d) a component storing the frequency-to-electrode maps; and (e) a display component displaying a visual representation of multiple frequency-to-electrode maps to facilitate a comparison between the frequency-to-electrode maps in making a determination by a user of a most desired frequency-to-electrode map.

23 Claims, 6 Drawing Sheets

COCHLEAR IMPLANT FITTING SYSTEM

PRIORITY CLAIM

This application is a Continuation-in-Part application of U.S. patent application Ser. No. 13/046,234 filed on Mar. 11, 2011 and entitled "Cochlear Implant Fitting System", which is a Continuation application of U.S. patent application Ser. No. 12/128,312 filed on May 28, 2008 entitled "Cochlear Implant Fitting System", now U.S. Pat. No. 7,908,012, which claims the priority to the U.S. Provisional Application Ser. No. 60/941,053, entitled "Cochlear Implant Fitting System," filed May 31, 2007. The specification of the above-identified applications are considered as being part of the disclosure of the present application and hereby expressly incorporated herewith by reference.

FIELD OF THE INVENTION

The present invention relates to a system and method for the electrical stimulation and frequency mapping of an installed cochlear implant.

BACKGROUND INFORMATION

Cochlear implants ("CI"s) may restore the ability to hear to deaf or partially deaf individuals by providing electrical stimulation to the auditory nerve via a series of electrodes placed in the cochlea. Sound input activates the electrodes of the CI with different frequency bands being assigned to the various electrodes based on the tonotopic organization of the inner ear. The placement of each electrode within the cochlea is related to the range and value of each frequency band, with electrodes closer to the base of the cochlea generally corresponding to higher frequency bands. CIs may successfully provide the ability of almost all postlingually deaf users (i.e., those who lost their hearing after learning speech and language) to gain an auditory understanding of an environment and/or restore hearing to a level suitable for an individual to understand speech without the aid of lipreading.

After the CI is put in place, sound is picked up by a microphone and sent via a speech processor of the CI to the electrodes. After implantation, it often takes an audiologist several months of fine-tuning (and it takes the patient several months of experience with the CI) before the full efficacy of the CI is reached. Even after programming has been completed, the distortion of auditory input associated with CI's (e.g., spectral degradation and frequency shift) often requires extensive perceptual learning on the part of the patient. Spectral degradation in the CI is caused by the limited number of stimulation channels while frequency shift results from physical limitations on the electrode insertion depth which may cause a mismatch between the speech processor's analysis filters and the characteristic frequency of the neurons stimulated by the electrodes.

Stimulation parameters for the CI include a frequency map which determines the electrodes to be stimulated in response to sound of a given frequency. Most patients undergoing electrical auditory stimulation are presented with a standard frequency map.

SUMMARY OF THE INVENTION

The present invention is directed to a system and method for the real-time electrical stimulation of a cochlear implant implanted in a patient. Furthermore, the present invention is directed to the creation of a frequency map containing the stimulation parameters for the patient, wherein the frequency map may be adjusted by a user of the system of the present invention in one of real time and with a short inter-stimulus interval while the CI is providing electrical stimulation to the patient.

The present invention is further directed to a method comprising adjusting baseline auditory stimulation parameters of a cochlear implant on a living body and providing auditory electrical stimulation to a living body via an electrode of the cochlear implant in combination with adjusting the auditory stimulation parameters of the cochlear implant to the living body in real time, retaining a database of used auditory stimulation parameters for a patient and selecting, in real time, from the database a desired one of the stimulation parameters that produces desired hearing percepts in a patient.

The present invention is further directed to a method comprising adjusting stimulation parameters in one ear that is being stimulated by a first cochlear implant while the other ear receives synchronized stimulation that is either electrical (e.g., provided by a second cochlear implant) or acoustic (e.g., provided by a hearing aid or through the patient's own unaided auditory system).

DETAILED DESCRIPTION

Figure 1:
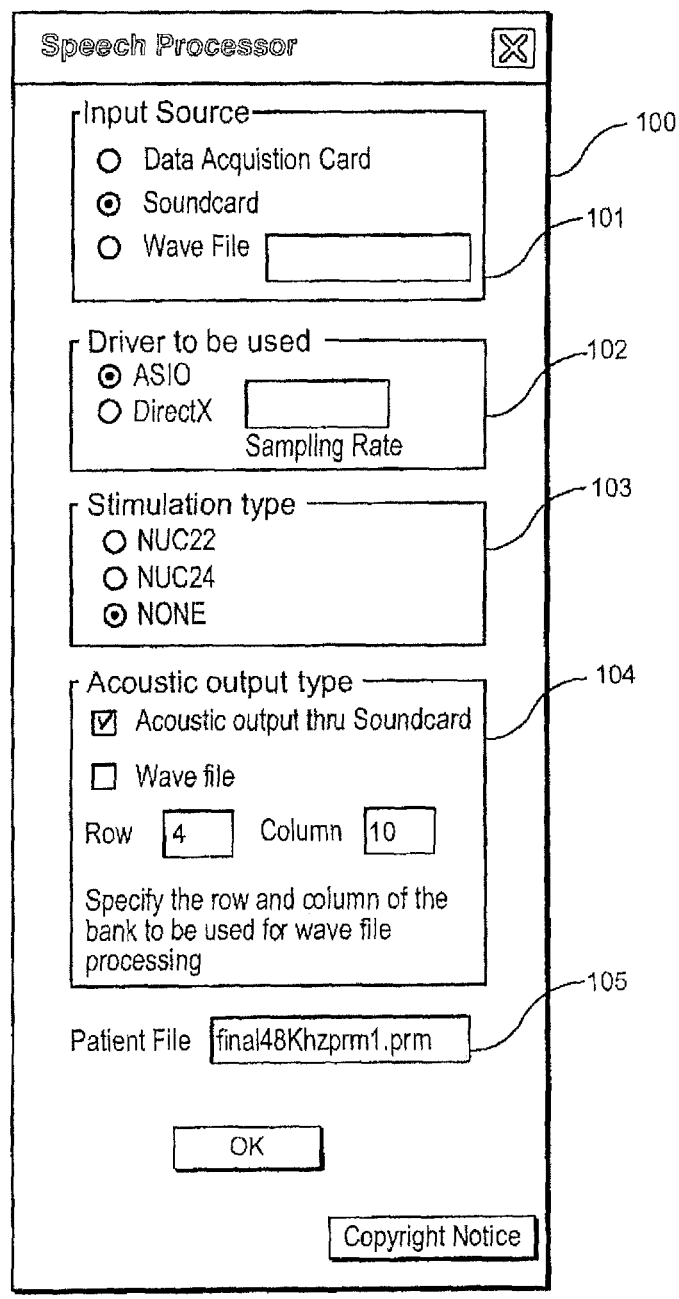
FIG. 1 shows an exemplary embodiment of an initial user interface of the present invention.

The present invention may be further understood with reference to the following description and the appended drawings. An exemplary embodiment of the present invention is directed to a system and method for providing stimulation information to a CI in real time, to facilitate the selection of a frequency-to-electrode map suited to the auditory requirements for a patient.

Under conventional CI techniques, several months are required for a patient to reach an asymptotic level of speech perception. As described above, conventional CIs distort auditory input due to frequency mismatch between the speech processor's analysis filters and the characteristic frequency of the stimulated neurons resulting from physical limitations in electrode insertion depth. In accordance with the exemplary embodiment of the present invention, a user of the CI is allowed to select a preferred frequency-to-electrode map, under the assumption that the user of the CI is best suited to select a frequency-to-electrode map minimizing frequency mismatch.

After implantation, audiologists often spend several months fine-tuning the CI before its full efficacy is reached. Each electrode in the CI may need to be fine-tuned to threshold listening levels separately. As each electrode is turned on, very small increases of electrical current are delivered to the hearing nerve until the patient hears a soft beep or tone. Once the softest hearing level is set, the patient listens for an increase in loudness until these beeps or tones become comfortable to hear. These steps are repeated in accordance with a general stimulation pattern until all electrodes have been set for soft and comfortable levels.

Since the characteristic frequencies for stimulated neurons cannot be measured noninvasively, the exemplary embodiment of the present invention seeks to identify these frequencies on an individual basis by creating individualized frequency-to-electrode maps during a real time electrical stimulation for each patient. The exemplary electrical stimulation may be provided with an interstimulus interval of zero or a value close to zero (e.g., less than 2 seconds). The ability to create individual frequency-to-electrode maps in real time is useful not only to reduce the time required for an audiologist to program a CI, but also to increase the efficacy of the CI by customizing its response to suit an individual's auditory capabilities. Furthermore, the exemplary embodiment of the present invention allows a patient to adjust parameters of the frequency-to-electrode map themselves during the stimulation process by adjusting a filter bank of the CI via a user interface, as will be described in greater detail below.

By subjecting the patient to specific sound frequencies, which, in turn elicit electrical activity in the CI, a proper frequency-to-electrode map is determined. Furthermore, by playing a succession of different sounds to the patient, the present invention enhances the accuracy of comparisons between different stimuli by minimizing the time between the stimuli to be compared such as during a flicker or interstimulus interval ("ISI") of 60-70 ms. For example, it is well known in the art that, in the auditory domain, the ability to discriminate between different speech sounds is significantly better when the ISI is 250 ms as opposed to an ISI of 2 sec. Similar results have also been obtained with non-speech sounds, as both frequency and intensity-discrimination thresholds are better with ISI's of 500 ms than with ISI's of 8 sec.

The widespread decrements in discriminability that occur with increasing ISI enable patients to compare different frequency maps significantly more accurately when they are presented with a series of frequency maps in a quick sequence while listening to running speech. One embodiment of the frequency mapping system of the present invention allows the comparison of dozens of frequency maps within minutes—at least an order of magnitude faster than the rate possible with available clinical tools. Another embodiment allows the presentation of the same speech stimulus processed using any two frequency-to-electrode tables chosen among dozens or hundreds of possible frequency-to-electrode tables, and with an ISI of less than 2 seconds between presentations. It is noted that the exemplary number of frequency-to-electrode tables may vary depending on any number of variables including, but not limited to, clinician preference, patient preference, patient requirements, etc. without deviating from the scope of the invention.

Furthermore, the exemplary embodiment of the present invention processes an acoustic auditory signal in real time and provides output in the form of acoustic stimulation patterns for the CI. Specifically, an input signal detected by the CI is separated into several frequency components using tools such as digital filtering, the Fast Fourier Transform or any other suitable means known to those skilled in the art. The amplitude of each of the separated frequency components is then used to determine the stimulation amplitude for waveforms sent to each electrode in the CI, and/or to determine the amplitude of noise bands that are used to acoustically simulate the auditory percepts of a CI patient.

The exemplary embodiment of the present invention allows a clinician, audiologist or CI user to change frequency maps associating acoustic frequency ranges to specific intracochlear electrodes in real time. Once a patient has recovered sufficiently after implantation of a CI, the frequency mapping method of the present invention may be employed. In accordance with the exemplary method, the initial execution may involve connecting the external portion of the CI to the appropriate stimulation hardware, as is well known to those skilled in the art. In the exemplary method described herein, the CI may be connected to a personal computer ("PC") or other suitable device whereby variables for the stimulation method may be programmed via a user-interface.

Once the CI has been connected to the PC, the audiologist selects and adjusts the parameters for the stimulation pattern. FIG. 1 shows an exemplary initial user interface 100 of a speech processor of the frequency mapping system according to the present invention. Initially, an audio input source may be selected by the audiologist from a first selection box 101. In an exemplary embodiment, the audiologist chooses between a selection of audio input sources (e.g., soundcard, data acquisition ("DAQ") card, wave file, etc.), as those skilled in the art will understand. The audio input source serves as a source of sound signals which are converted to the electrical stimulation signals sent to the electrodes of the CI. A second selection box 102 allows the audiologist to select a driver to be used where necessary for analog to digital ("A/D") and/or digital to analog ("D/A") conversion. In the exemplary embodiment shown, the audiologist may select between an Audio Stream Input Output ("ASIO") driver, and a DirectX driver. Those skilled in the art will understand that any suitable driver that provides an interface between the speech processor and the sound input source of the PC may be used. The audiologist may then select a sampling rate for the input signal as will be described in greater detail below.

The audiologist may now select the stimulation type for the procedure from a third selection box 103. The stimulation type determines whether stimulation data will be sent to the CI. In the exemplary embodiment shown, a user may select to stimulate one of two different CIs, NUC 22 and NUC24 indicative of the type of cochlear implant the patient may have. Alternatively, the audiologist may select not to stimulate either ear, such as when testing is being performed. When this button is selected, no output is sent to the CI.

The audiologist may then select an acoustic output type from a fourth selection box 104. For example, the audiologist may send the acoustic output to disk by selecting the "Wave file" option or play the acoustic output through the sound card by selecting the "Acoustic output through Soundcard" option.

The audiologist may also select the row and column of the filter bank frequency-to-electrode map for the stimulation. The speech processor of the present invention may load a large number of frequency-to-electrode maps, with each frequency-to-electrode map organized in a matrix by row and column and with each position in the matrix being representative of a different frequency-to-electrode map. When the speech processor is used in an offline mode (i.e., where the acoustic output type is a wave or other sound file) the row and column boxes indicate which frequency-to-electrode map will be used. When the program is used in a real time mode (i.e., one of the soundcard, DAQ card, etc. is selected as the input source), the row and column boxes indicate the initial frequency-to-electrode map to be used when the stimulation commences. Accordingly, in the exemplary method of the present invention, the audiologist or the patient or any other operator of the system may move around the matrix of frequency-to-electrode maps and change frequency-to-electrode map selections in real time.

Lastly, the audiologist may select a patient file to load from a fifth selection box 105. The patient file contains parameters specific to a patient including, but not limited to, a stimulation strategy, frequency-to-electrode map, a stimulation rate, channels to be stimulated, input dynamic range as well as threshold and comfortable electrical stimulation levels for each channel. The patient file may store the aforementioned files by date and instance of stimulation. For example, a user may save parameters to the patient file each time a stimulation is performed. The audiologist may also reference the file to determine how many stimulations have been performed on a patient as well the specific parameters used in each stimulation.

Figure 2:
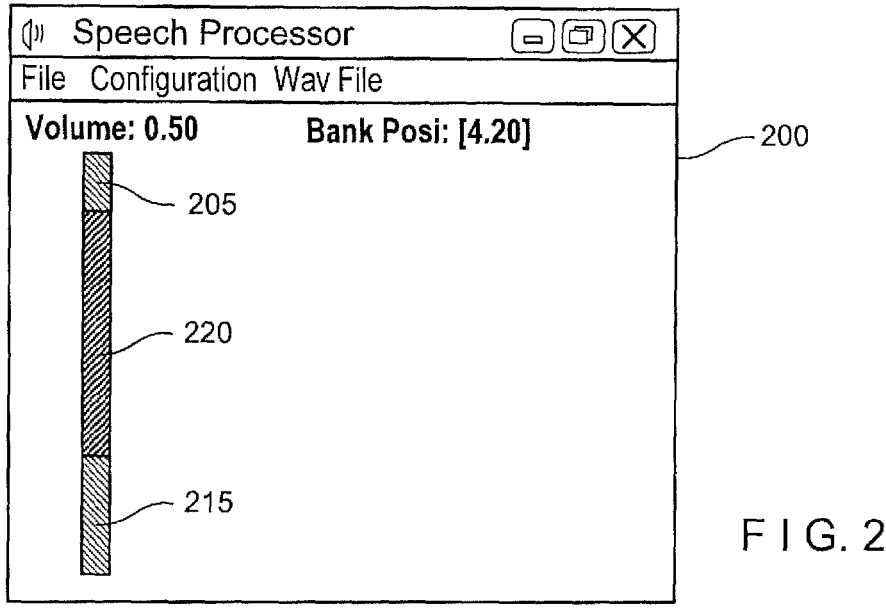
FIG. 2 shows an exemplary embodiment of the user interface for filter bank adjustment of the present invention.

FIG. 2 shows an exemplary embodiment of an initial screen an audiologist or patient may see at the beginning of a frequency-to-electrode map adjustment task. A dark rectangle 220 represents the frequency range covered by the active frequency-to-electrode map, whose output is heard by the patient in real time. In an exemplary embodiment, the frequency-to-electrode map bank covers frequencies ranging from 850 Hz to 17,000 Hz. Employment of a large number of frequency-to-electrode maps allows the audiologist to select ranges best suited for the patient's auditory capabilities. The dark rectangle 220 plus the two additional rectangles 205 and 215 in a lighter color, placed above and below the dark rectangle 220 respectively, represent the total frequency range audible to humans. One possible frequency scale that may be used for this graphical representation is determined by Greenwood's Function, which states that frequency is a function of the specific location within the cochlea. In other words, the length of each of the rectangles represents a distance along the cochlea.

During the stimulation, the patient or audiologist uses a keyboard or other suitable interface of the PC to change the active frequency-to-electrode map indicated by the dark rectangle 220. Appropriate controls such as, for example, the arrow keys on a computer keyboard, may be used to increase or decrease the frequency range of the frequency-to-electrode map (i.e., the length of the dark rectangle 220), while leaving the midpoint constant. Such a change may show up in the display as either an expansion or a contraction of the dark rectangle 220. Alternate controls may be used to move the entire active frequency-to-electrode map up or down in frequency while leaving the extent of the frequency range constant. In this case, the dark rectangle 220 may be moved up or down in the display while its length remains constant. The capability to change the extent and/or the mid-point of the frequency range during stimulation provides a greater degree of accuracy and efficiency than afforded by currently available systems. It is also possible to use other controls to change other characteristics of the frequency-to-electrode map (e.g., the lowest frequency edge of the whole map, the highest frequency edge of the whole map, the distribution of frequency bands within the whole frequency range, etc.), not just the extent and mid-point of the frequency range.

The dark rectangle 220 which is representative of the entire frequency-to-electrode map relative to the chosen stimulation parameters may be subdivided into a number of frequency subranges, with each subrange being indicative of a filter in the frequency-to-electrode map. In an exemplary embodiment, a range of 8 to 22 filters may be used in the frequency-to-electrode map. However, it is noted that this is only an exemplary embodiment and, in function, any number of plurality of filters may be used.

It is noted that, while an operator of the system changes the frequency-to-electrode map, speech processing continues without perceptible interruption. Therefore, the patient may make immediate and precise assessments concerning the relative intelligibility and sound quality of the various frequency-to-electrode maps tested. Using such a system increases accuracy and reduces perceptual problems that may be caused by using larger ISIs in the stimulation, as discussed earlier. As those skilled in the art will understand, employment of a system wherein a continuous acoustic or electrical stimulation is used, the ISI is substantially reduced to zero.

Figure 3:
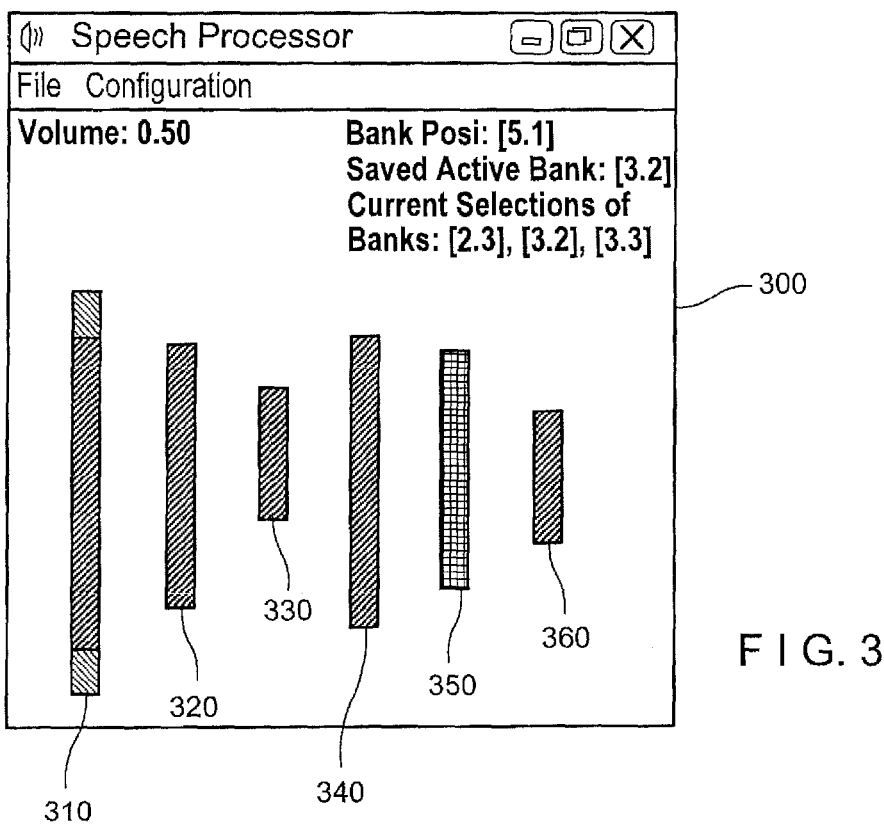
FIG. 3 shows an exemplary embodiment of the user interface for filter bank adjustment of the present invention after several filter banks have been selected and one of them is active.

In addition to the continuous adjustment described above, the patient or audiologist may also select a number of frequency-to-electrode maps for further comparison. For example, as shown in FIG. 3, after a user of the speech processor has selected a frequency-to-electrode map 320 in accordance with the procedure noted above, the frequency-to-electrode map 320 may be placed on a screen alongside a real-time frequency-to-electrode map adjuster 310, as shown in FIG. 3. This procedure may be repeated with any plurality of frequency-to-electrode maps, such as frequency-to-electrode maps 330-360. A user of the speech processor of the present invention may align the plurality of frequency-to-electrode maps 320-360 on one window using a simple copying technique (e.g., by making a selection from a drop-down menu or other means known in the art). Alternatively, the plurality of frequency-to-electrode maps 320 -360 may be added automatically on an individual basis once a frequency-to-electrode map has been chosen. This may allow a user of the speech processor to quickly and accurately compare the plurality of frequency-to-electrode maps to discover what changes may enhance the performance of the CI.

The availability of the real-time frequency-to-electrode map adjuster allows an operator of the system to customize a frequency-to-electrode map incorporating any desired changes identified during the testing procedure. The operator may scroll through the plurality of frequency-to-electrode maps 310-360 via the user interface of the PC such as, for example, by pressing the space bar. The active frequency-to-electrode map may be highlighted by any of a number of means such as with a border or color change of the frequency-to-electrode map, as is shown with respect to the active frequency-to-electrode map 350 in FIG. 3.

Figure 4:
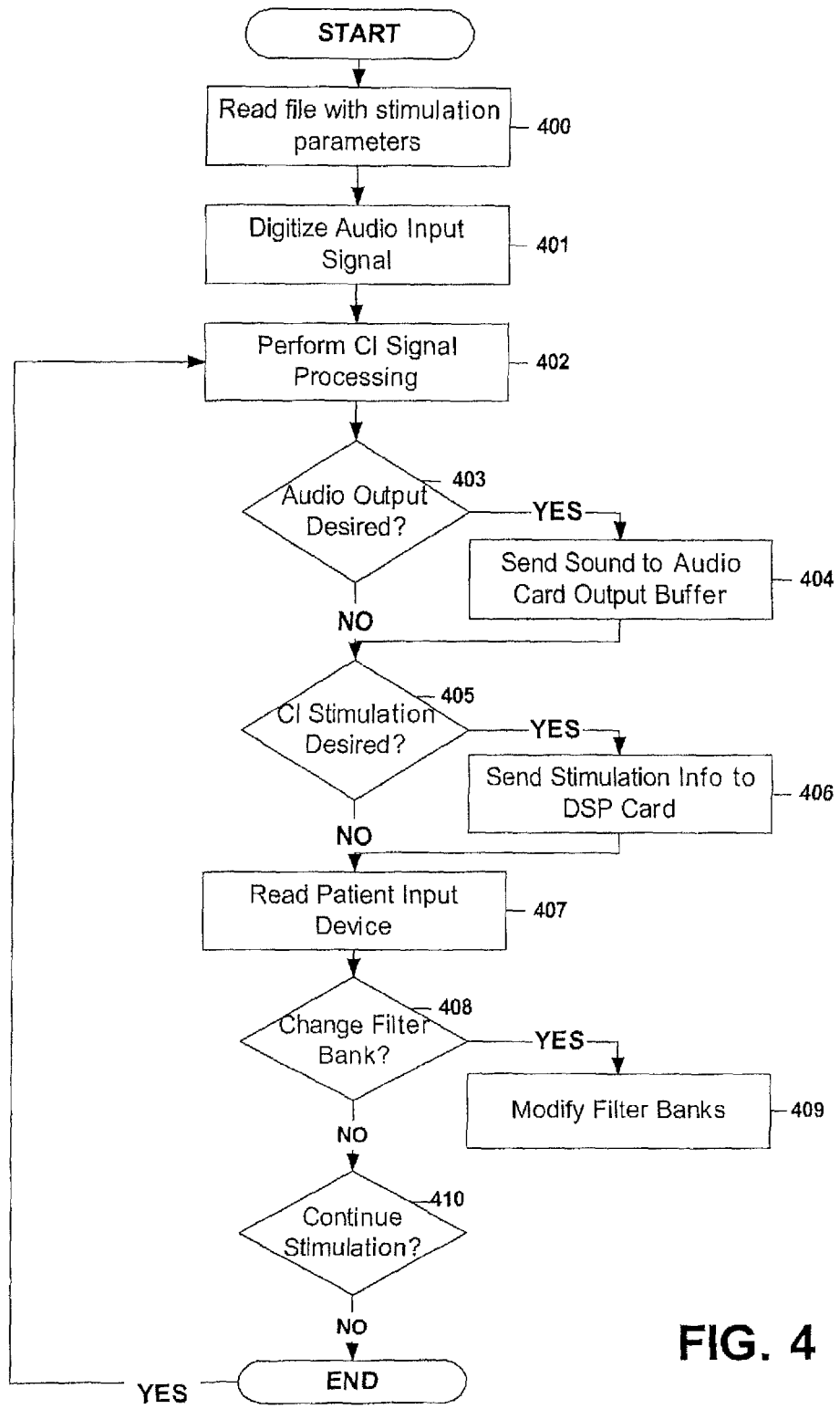
FIG. 4 shows an exemplary embodiment of a method according to the present invention.

An exemplary method of the present invention as described with respect to FIG. 4 begins by allowing an operator of the system to select a patient file to begin stimulation. In step 400, a user interface based on a PC or other data processing apparatus may be used to read the patient file which stores parameters for the stimulation. These parameters may include, but are not limited to, stimulation strategy, frequency-to-electrode map, minimum and maximum stimulation levels for each channel, stimulation rate, input dynamic range, filters for filter banks, etc. In step 401, the system begins digitizing the audio input signal produced based on the stimulation parameters provided by an operator.

In step 402, the system of the present invention begins CI signal processing including, for example, making determinations of stimulus pulse amplitudes, filtering or frequency transform calculations, automatic gain control, pre-emphasis, etc., as those skilled in the art will understand. A parameter read during step 400 determines if audio output is desired in step 403. As described above, the operator may not desire audio output and in this case the method proceeds to step 405. However, if the operator elects to have audio output, the method continues to step 404, where the sound signal is sent to the audio card output buffer of the system, as those skilled in the art will understand.

The method then proceeds to step 405, in which the operator decides whether CI stimulation is desired, as also described earlier. If the operator elects to use CI stimulation, such as when a real-time stimulation is being performed, the method proceeds to step 406, wherein the stimulation is sent to an appropriate interface which may be based on a Digital Signal Processor ("DSP") card and may include additional hardware depending on the specific cochlear implant used by the patient. The DSP card provides real-time digital signal processing of the audio signal, as those skilled in the art will understand. The output of the interface including the DSP Card is connected to a transmitter coil placed on the patient's head. This coil transmits stimulation information to the implanted device. If no CI stimulation is desired, the method may proceed to step 407, wherein the system reads the user interface device such as the PC to determine whether changes have been made to the stimulation parameters during the real-time stimulation. Because the present invention operates in real-time, any changes made to the parameters are immediately reflected in the stimulation.

Step 408 determines if any changes have been made to the filter bank, as shown with respect to FIGS. 2 and 3. If no changes have been made, the method may continue. If changes have been made, the filter banks in the system are updated to reflect the change in step 409. The operator decides whether to stop stimulation by providing an appropriate instruction to the program. Unless the operator decides to stop, the method returns to step 402 wherein CI signal processing continues. Otherwise, if the operator elects not to continue processing, the method ends.

Figure 5:
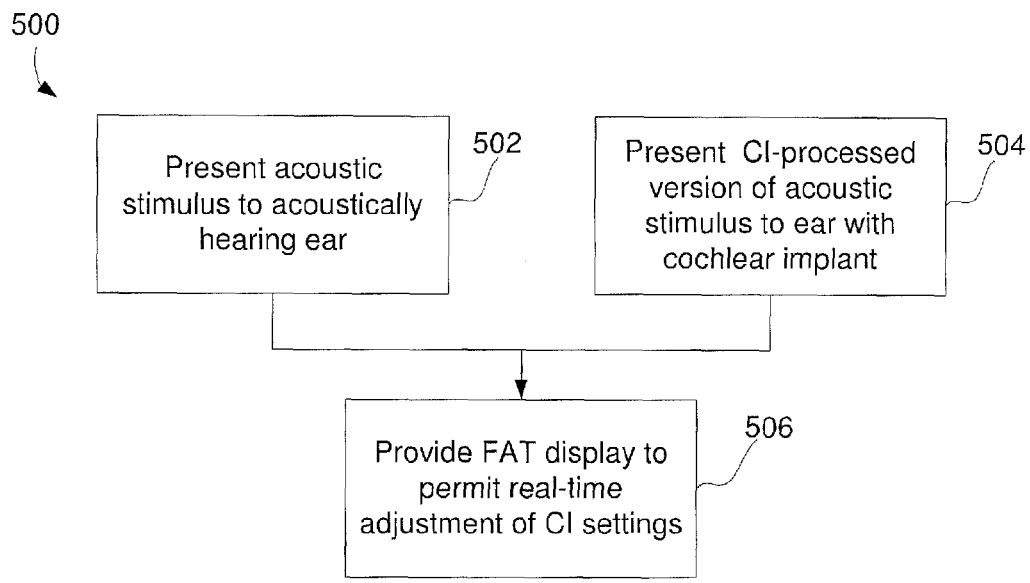
FIG. 5 shows an exemplary method according to another embodiment of the invention.
Figure 6:
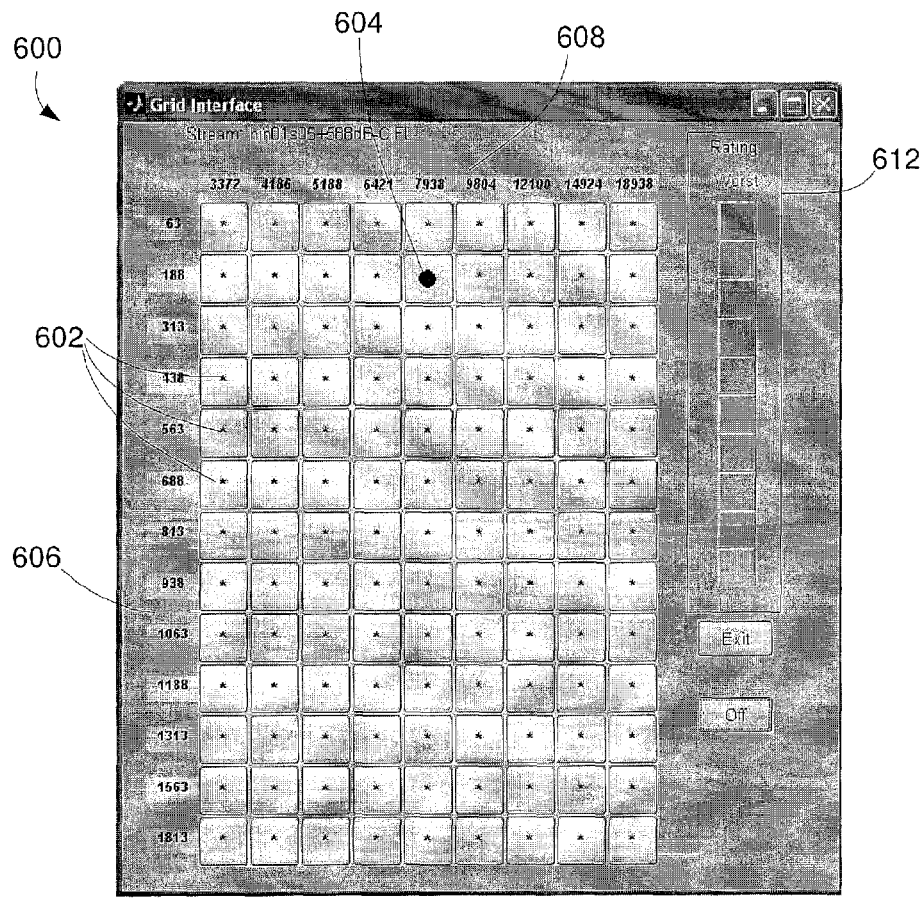
FIG. 6 shows a FAT grid display according to the invention.
Figure 7:
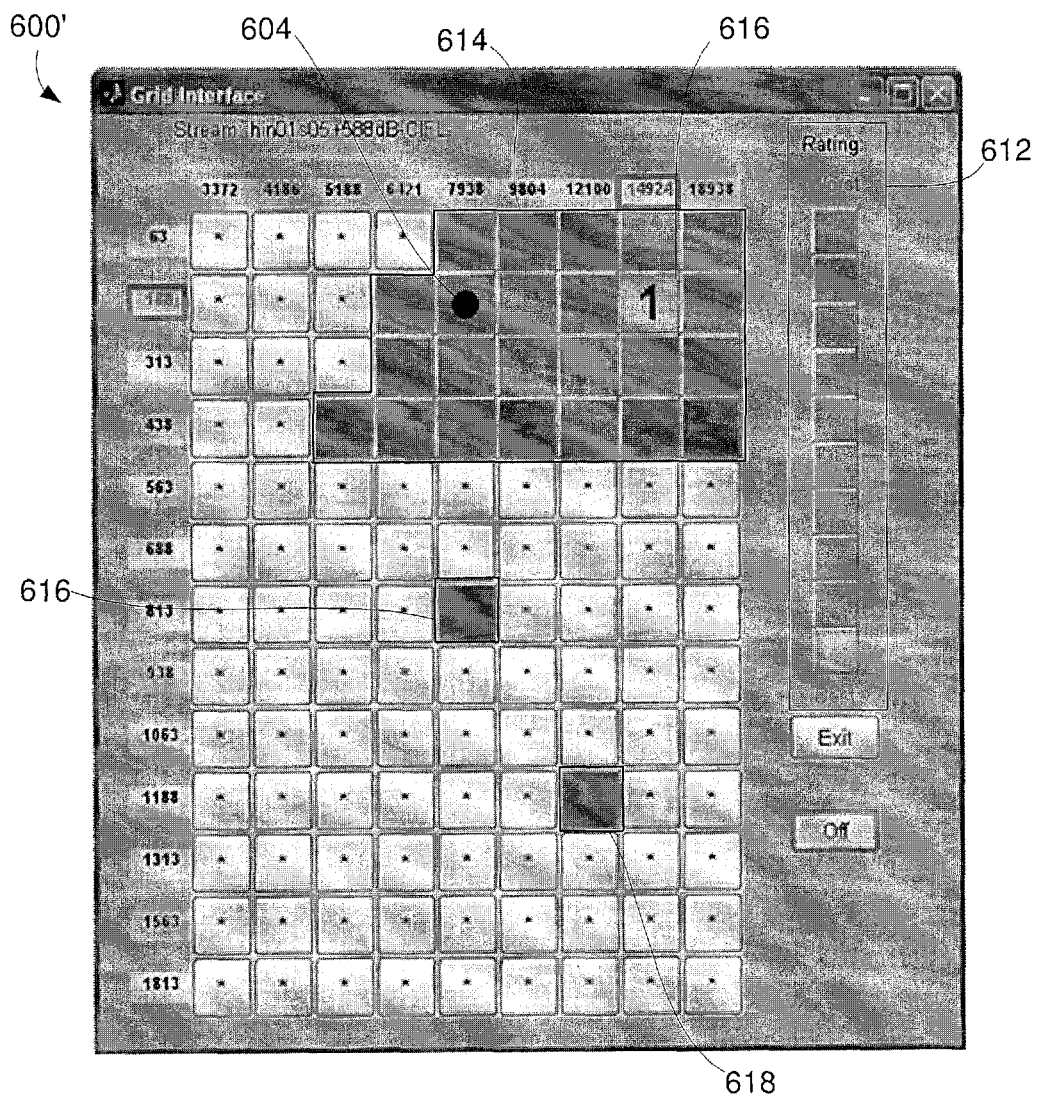
FIG. 7 shows a user-specific FAT grid display according to the invention.

FIGS. 5 and 7 depict methods according to another embodiment of the invention, wherein an exemplary cochlear implant fitting system may be employed for the fitting of an implant in patients who have some degree of hearing in each ear. Specifically, as those skilled in the art will understand, conventional cochlear implant fitting systems are directed to patients who are profoundly or totally deaf or have only a single cochlear implant. However, for patients who are either bimodal, who use a cochlear implant in one ear and hear acoustically through the other ear (e.g., sometimes with the help of a conventional hearing aid), or for patients who are bilateral, having limited hearing in both ears, each of which is fitted with a cochlear implant. The exemplary system and method according to the invention permits synchronized stimulation of both ears with stimuli selected to correspond to the hearing percepts of the corresponding ear, as will be described in greater detail hereinafter. The system and method according to the invention further allows a patient to hear speech processed with different frequency allocation tables (FAT's) to make perceptual comparisons with short ISI's while providing to a patient or audiologist access to a wide range of different FAT's. An ISI for the system and method according to the invention is less than two seconds or, in another embodiment, as close as possible to zero, thus aiding a patient in making an assessment between different FAT's.

FIG. 5 depicts a method 500 according to a first embodiment directed toward patients having bimodal hearing. In a first step 502, an acoustic stimulus is provided to the acoustic ear, which may be fitted with a hearing aid. In step 504, which is carried out simultaneously with step 502, a CI-processed version of the acoustic stimulus is presented to the other ear, which is fitted with the cochlear implant. That is, the exemplary method 500 is directed to providing two separate signals simultaneously to both ears, wherein the two signals may or may not include the same stimulation settings. For example, an acoustic signal may be sent to the acoustic ear and a corresponding CI signal (i.e., a signal processed using a FAT which is selected by the patient as described below) is sent to the CI ear. Thus, the implant fitting system of the method 500 allows a patient to hear stimuli in both ears at the same time, mimicking a real-world environment. In a next exemplary step 506, a display 600 is provided to the patient displaying a plurality of frequency allocation tables (FAT' s) 602 which may be selected by the patient to provide real-time adjustment of the settings of the cochlear implant and a selected FAT 604 corresponding to a most perceptually appropriate hearing setting for the patient when hearing with both ears.

The exemplary display 600 according to the invention displays a plurality of FAT's 604 ranging from lower frequencies along a vertical column 606 to higher frequencies along a horizontal column 608. In an operative configuration, a patient or other user may select a different FAT based on a perceptual criterion such as, for example, an FAT which results in the most intelligible speech or an FAT which results in the most natural-sounding speech. The FAT may optionally be named based on clinician or patient input and selected via the display 600. Furthermore, the exemplary system and method according to the invention are provided with a rating system 612 which stores to a memory a rating assigned by the user to each FAT. Specifically, once the user has selected an FAT 604, a rating may be assigned thereto using the rating scale 612. The selected rating may be stored in the memory and displayed on the display via, for example, a change in color or any other display setting (e.g., change in size, shape, outline, font, etc, of the selected FAT 604 box). The selected setting may further be stored on the memory for future reference. Specifically, as shown in FIG. 7, a user-specific FAT display 600' may be generated to correspond to patient ratings of the FAT's, wherein the user-specific display 600' may be modified by the patient at any time. As those skilled in the art will understand, the user-specific display 600' streamlines a future selection of an FAT by displaying to the user previously rated efficacies for each rated FAT. This provides a general guideline of a most perceptually appropriate range of frequencies for the user to aid in selection of a most perceptually appropriate FAT. The user-specific display 600', for example, depicts a first region 614 color coded to indicate which FAT's have been previously rated. As noted above, any other coding means may be used without deviating from the scope of the invention. In this first region, FAT 616 was rated the most perceptually appropriate, as indicated by a color thereof. Second and third regions 616, 618 were also previously rated with a color thereof indicating that they were assigned a negative rating. Thus, the user, when making seeking a most perceptually appropriate FAT, may select an FAT in the range of the first region 614 based on its previous rating. Alternatively, the user may also choose to ignore previously used ratings in making a current determination. In this case, the previous ratings may optionally be omitted from the display. In another embodiment, the user may toggle between the display 600 and the display 600' in selecting a current FAT.

Figure 8:
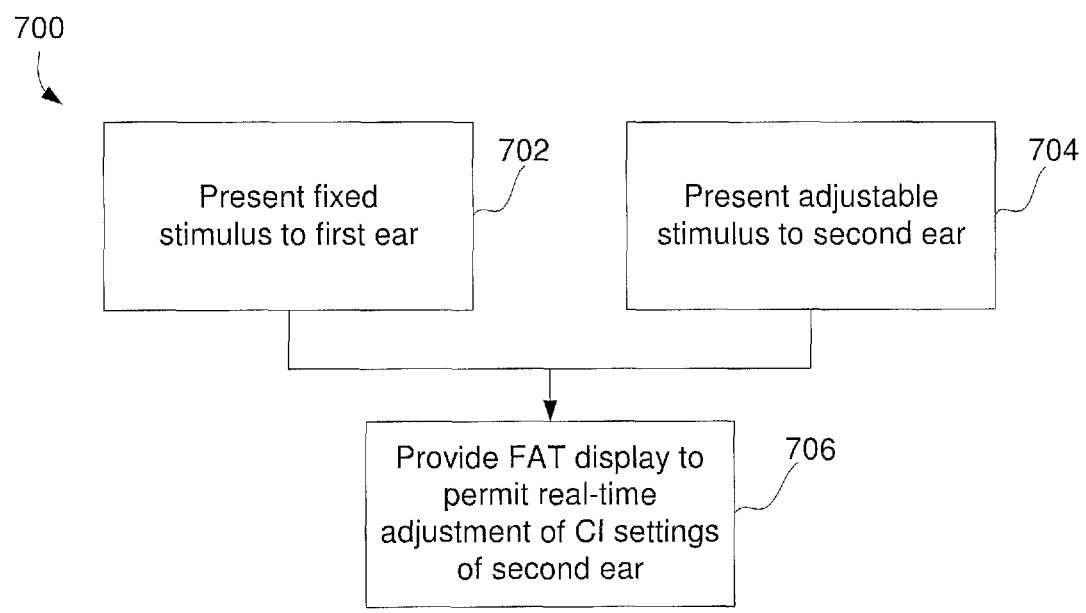
FIG. 8 shows an exemplary method according to yet another embodiment of the invention.

FIG. 8 depicts a method 700 according to another embodiment of the invention, wherein stimulation is provided to a patient with bilateral hearing concerns for which the patient is being fitted with a cochlear implant in each ear. In a first exemplary step 702, a fixed stimulus provided to a first ear corresponds to any of (1) a previously selected perceptually appropriate stimulus for the first ear, (2) a standard FAT used for a majority of patients (e.g., having a low frequency edge of 188 Hz and a high frequency edge of 7938 Hz, etc.) and (3)

any user/clinician selected FAT. In step 704, which is carried out simultaneously with step 702, an adjustable stimulus is provided to the second ear at an initial value corresponding to the value provided to the first ear or at a value selected in accordance with any of the conditions noted above. In a next step 706, the display 600 is provided to the patient, the display displaying a plurality of frequency allocation tables (FAT's) 602 which may be selected by the patient to provide for real-time adjustment of the settings of the cochlear implant of only the second ear with a selected FAT 604 corresponding to a most perceptually appropriate hearing setting for the patient when hearing with both ears. In another embodiment, both CI settings may be adjustable—e.g., via two different FAT displays provided on one screen. It is noted that although the description is described with respect to frequency allocation tables, any other stimulation parameters may be adjusted according to the system and method disclosed herein without deviating from the scope of the invention.

The exemplary system and method described herein provides a computer program product to be loaded by a computer arrangement, the computer program comprising instructions for providing stimulation to one or both ears in accordance with one of previously identified and real-time adjustable instructions. The computer program may comprise a processing unit and a memory, the computer program product, after being loaded, providing said processing unit with the capability to carry out steps of the method. The computer program may include, as a separate software module, as a combination of hardware and software. For example, the software module may be a program containing lines of code that, when compiled, may be executed on a processor.

The exemplary embodiment of the present invention may be used by patients who have one cochlear implant, with or without residual hearing, and patients who use bilateral cochlear implants. Other embodiments of the invention will be apparent to those skilled in the art from consideration of the specification and practice of the invention disclosed herein. Thus, it is intended that the present invention cover the modifications and variations of this invention provided they come within the scope of the appended claims and their equivalents.

What is claimed is:

1. A method, comprising:
   displaying a visual representation of a plurality of frequency-to-electrode maps for selection by a user, the visual representation configured to facilitate a comparison between patient responses to auditory stimulation having parameters corresponding to each of the frequency-to-electrode maps;
   providing a first auditory stimulation to a first ear of a patient having a first cochlear implant, wherein parameters of the first auditory stimulation correspond to a first frequency-to-electrode map selected by the user using the visual representation, and the first auditory stimulation is electrical;
   obtaining from the patient, in real-time, ratings corresponding to hearing percepts of the patient in response to the first selected frequency-to-electrode map; and
   adjusting, within an interstimulus interval of 2 seconds or less, the parameters of the first auditory stimulation to the first ear to correspond to a second frequency-to-electrode map selected by the user using the visual representation.

2. The method of claim 1, further comprising retaining a database comprising the frequency-to-electrode maps selected by the user and corresponding ratings retrieved from the patient.

3. The method of claim 1, further comprising providing a second auditory stimulation to a second ear simultaneously with the first auditory stimulation.

4. The method of claim 3, wherein the second ear is fitted with a second cochlear implant and wherein the second auditory stimulation is electrical.

5. The method of claim 4, wherein the parameters of the first auditory stimulation are same as or different from parameters of the second auditory stimulation.

6. The method of claim 3, wherein the second ear hears acoustically, the second ear being one of fitted with a hearing aid and not fitted with a hearing aid, wherein the second auditory stimulation is acoustical.

7. The method of claim 6, wherein the first auditory stimulation is a CI-processed version of the second auditory stimulation.

8. The method of claim 3, wherein the patient has bimodal or bilateral hearing.

9. The method of claim 1, wherein parameters of the second auditory stimulation are fixed.

10. The method of claim 1, wherein the parameters of the first auditory stimulation is adjustable in real time.

11. The method of claim 1, further comprising:
    obtaining from the patient, in real-time, ratings corresponding to hearing percepts of the patient in response to the second frequency-to-electrode map;
    repeating the adjusting step and the second obtaining step for each additional frequency-to electrode map selected by the user using the visual representation; and
    selecting based on the ratings a desired one of the frequency-to-electrode maps that produces desired hearing percepts in a patient.

12. A system for electrically stimulating a first cochlear implant, comprising:
    a first transmitter transmitting a first electrical stimulus from a stimulation hardware to a first cochlear implant configured to be fitted in a first ear of a patient;
    a component establishing a plurality of frequency-to-electrode maps, each frequency-to-electrode map corresponding to a set of stimulation parameters for the first electrical stimulus provided by the stimulation hardware;
    a display component displaying a visual representation of the plurality of frequency-to-electrode maps for selection by a user, the visual representation configured to facilitate a comparison between patient responses to auditory stimulation corresponding to the frequency-to-electrode maps; and
    a user-interface component permitting a user to adjust, within an interstimulus interval of 2 seconds or less, parameters of the first electrical stimulus to correspond to the frequency-to-electrode maps selected by the user, and to provide, in real-time, ratings corresponding to hearing percepts of the patient in response to auditory stimulation corresponding to the selected frequency-to-electrode maps.

13. The system of claim 12, further comprising a memory unit storing the selected frequency-to-electrode maps and corresponding ratings for the patient.

14. The system of claim 12, further comprising
    a second transmitter simultaneously transmitting with the first electrical stimulus a second stimulus from the stimulation hardware to a second ear, the second stimulus being one of electrical and acoustical.

15. The system of claim 14, wherein the second ear is fitted with a second cochlear implant.

16. The system of claim 14, wherein parameters of the second stimulation are fixed.

17. The system of claim 14, wherein the first electrical stimulation is a CI-processed version of the second stimulation.

18. The system of claim 12, wherein the parameters of the first electrical stimulation are same as or different from parameters of the second stimulation.

19. A non-transitory computer readable storage medium including instructions which, when executed by a processor, directs the processor to perform the following steps:
   displaying a visual representation of a plurality of frequency-to-electrode maps for selection by a user, the visual representation configured to facilitate a comparison between patient responses to auditory stimulation having parameters corresponding to each of the frequency-to-electrode maps;
   providing a first auditory electrical stimulation to a first ear of a patient fitted with a first cochlear implant, wherein parameters of the first auditory stimulation corresponds to a first frequency-to-electrode map selected by the user using the visual representation;
   obtaining from the patient, in real-time, ratings corresponding to hearing percepts of the patient in response to auditory stimulation corresponding to the selected frequency-to-electrode maps; and
   adjusting, within an interstimulus interval of 2 seconds or less, the parameters of the first auditory stimulation to the first ear to correspond to a second frequency-to-electrode map selected by the user using the visual representation.

20. The non-transitory computer-readable storage medium of claim 19, further comprising storing on a memory the selected frequency-to-electrode maps and corresponding ratings for the patient.

21. The non-transitory computer-readable storage medium of claim 19, wherein the instructions which, when executed by the processor, further directs the processor to provide a second auditory stimulation to a second ear simultaneously with the first auditory stimulation.

22. The non-transitory computer-readable storage medium of claim 21, wherein the instructions which, when executed by the processor further directs the processor to adjust parameters of the second auditory stimulation parameters.

23. The non-transitory computer-readable storage medium of claim 19, wherein the instructions which, when executed by the processor, further directs the processor to:
   obtain from the patient, in real-time, ratings corresponding to hearing percepts of the patient in response to the second frequency-to-electrode map;
   repeat the adjust step and the second obtain step for each additional frequency-to electrode map selected by the user using the visual representation; and
   select based on the ratings a desired one of the frequency-to-electrode maps that produces desired hearing percepts in a patient.

* * * * *